(12) United States Patent
Yang

(10) Patent No.: US 6,468,250 B2
(45) Date of Patent: Oct. 22, 2002

(54) DUAL-CHAMBER SAFETY HYPODERMIC SYRINGE

(76) Inventor: Kuo-Chen Yang, 2F., No. 2, Lane 21, Alley 34, Chung-Hsiao St., Yungho City, Taipei Hsien (TW)

( * ) Notice: Subject to any disclaimer, the term of this patent is extended or adjusted under 35 U.S.C. 154(b) by 1 day.

(21) Appl. No.: 09/745,931

(22) Filed: Dec. 26, 2000

(65) Prior Publication Data

US 2002/0082560 A1 Jun. 27, 2002

(51) Int. Cl.[7] ................................................. A61M 5/32
(52) U.S. Cl. ...................... 604/198; 128/919; 604/220; 604/240
(58) Field of Search ................ 604/93.01, 181–183, 604/186–188, 191–192, 194–195, 197–198, 207, 214–215, 218, 220–221, 231, 240, 243, 264, 272, 82, 110; 128/919

(56) References Cited

U.S. PATENT DOCUMENTS

| | | | | |
|---|---|---|---|---|
| 4,941,883 A | * | 7/1990 | Venturini ..................... | 604/125 |
| 5,263,942 A | * | 11/1993 | Smedley et al. ............. | 604/110 |
| 5,298,023 A | * | 3/1994 | Haber et al. ................. | 604/191 |
| 5,300,038 A | * | 4/1994 | Haber et al. ................. | 604/187 |
| 5,498,245 A | * | 3/1996 | Whisson ...................... | 128/919 |
| 5,514,107 A | * | 5/1996 | Haber et al. ................. | 604/192 |
| 5,709,667 A | * | 1/1998 | Carilli ......................... | 604/110 |
| 5,728,073 A | * | 3/1998 | Whisson ...................... | 604/194 |

* cited by examiner

Primary Examiner—Anhtuan T. Nguyen
Assistant Examiner—LoAn H. Thanh
(74) Attorney, Agent, or Firm—Bacon & Thomas, PLLC

(57) ABSTRACT

A dual-chamber safety hypodermic syringe. The syringe includes a barrel having a medicine chamber, a needle chamber, and a guide hole connected between the chambers. The needle assembly is moved in and out of the needle chamber between the extended position where an inlet on a neck of the needle assembly is disposed in communication with the guide hole for enabling liquid medicine to be squeezed out from the medicine chamber through the needle cannula of the needle assembly, and the received position where the needle assembly is safely received inside the needle chamber and kept from sight.

9 Claims, 4 Drawing Sheets

DUAL-CHAMBER SAFETY HYPODERMIC SYRINGE

BACKGROUND OF THE INVENTION

1. Field of the Invention

The present invention relates to a safety hypodermic syringe and, more particularly, to a dual-chamber safety hypodermic syringe, which is suitable for use to inject medicine into the body as well as to draw blood from the body, and enables the needle cannula to be safely received in an independent needle chamber after its service.

2. Description of Related Art

In regular safety hypodermic syringes, the plunger has catch means at the front side for catching the needle assembly. After the plunger had been pushed to the front side to squeeze medicine out of the barrel, the catch means is forced into engagement with the needle hub of the needle assembly. Therefore, the needle assembly is pulled backwards and received inside the barrel after a backstroke of the plunger. However, when the user pulls the plunger to the rear limit position, the plunger protrudes over the rear side of the barrel at a distance, and the length of the hypodermic syringe is relatively increased. Because the front side of the barrel is kept in an open status, the needle cannula tends to be forced out of the barrel again when hitting the plunger against an object accidentally. In order to eliminate this problem, another prior art may employ much effort forwards to the plunger to curve the metal needle cannula after the needle assembly has been moved backwards with the plunger inside the barrel. However, the needle cannula may be forced to pierce through the peripheral wall of the barrel when employing force forwards to the plunger to curve the needle cannula. There is still one another structure of safety hypodermic syringe, in which the plunger is broken and plugged into the front opening of the barrel again to curve the needle cannula of the needle assembly after the needle assembly had been received inside the barrel. However, it requires much effort to plug the plunger into the front opening of the barrel against the metal needle cannula and to curve the metal needle cannula, and an accident of piercing through the peripheral wall may still occur when curving the metal needle cannula.

Further, in order to prevent engagement of the catch means of the plunger with the needle hub of the needle assembly before the use of the safety syringe, a gap must be maintained between the plunger and the needle hub of the needle assembly. However, the presence of the gap causes the safety hypodermic syringe unable to be used to draw blood from the body. This design also causes a high cost of packing material to keep the gap in distance.

Therefore, it is desirable to provide an improved hypodermic syringe to mitigate and/or obviate the aforementioned problems.

SUMMARY OF THE INVENTION

The main object of the present invention is to provide a dual-chamber safety hypodermic syringe, which enabling the needle assembly to be safely received in an independent needle chamber after its service, and preventing the needle cannula from being pushed forwardly or piercing sideways to the outside of the barrel to injure people by an accident. Another object of the present invention is to provide a dual-chamber safety hypodermic syringe, which is practical for use to inject medicine into the body as well as to draw blood from the body.

To achieve the object, the dual-chamber safety hypodermic syringe of the present invention includes a needle assembly, the needle assembly comprising a needle hub and a needle cannula mounted in the needle hub, the needle hub comprising a neck on the middle and an inlet on the neck in communication with the needle cannula, and a handle extended sideways from the periphery thereof; and a barrel, the barrel comprising a front side, a rear side, a medicine chamber and a needle chamber respectively extended in axial direction, an outlet in the front side of the barrel, the needle chamber having a front open side connected to the outlet and a rear open side extended through the rear side of the barrel, the medicine chamber having a closed front side and a rear open side extended to through the rear side of the barrel, a guide hole communicated between the medicine chamber and the needle chamber, a longitudinal sliding slot disposed in parallel to and in communication with the needle chamber, and a front retaining hole extended sideways from a front end of the longitudinal sliding slot; wherein the needle assembly is slidably mounted in the needle chamber such that when the handle is moved forwards along the longitudinal sliding slot and engaged into the front retaining hole, the needle assembly is locked in an extended position to hold the needle cannula outside said barrel and to keep the inlet in communication with the guide hole for enabling a liquid medicine or blood to pass through the medicine chamber, the guide hole, the inlet and the needle cannula. After the service of the safety hypodermic syringe, the handle is disengaged from the front retaining hole and then moved along the longitudinal sliding slot needle in the reversed direction to receive the needle assembly safely inside the needle chamber.

Other objects, advantages, and novel features of the invention will become more apparent from the following detailed description when taken in conjunction with the accompanying drawings.

DETAILED DESCRIPTION OF THE PREFERRED EMBODIMENT

Figure 1:
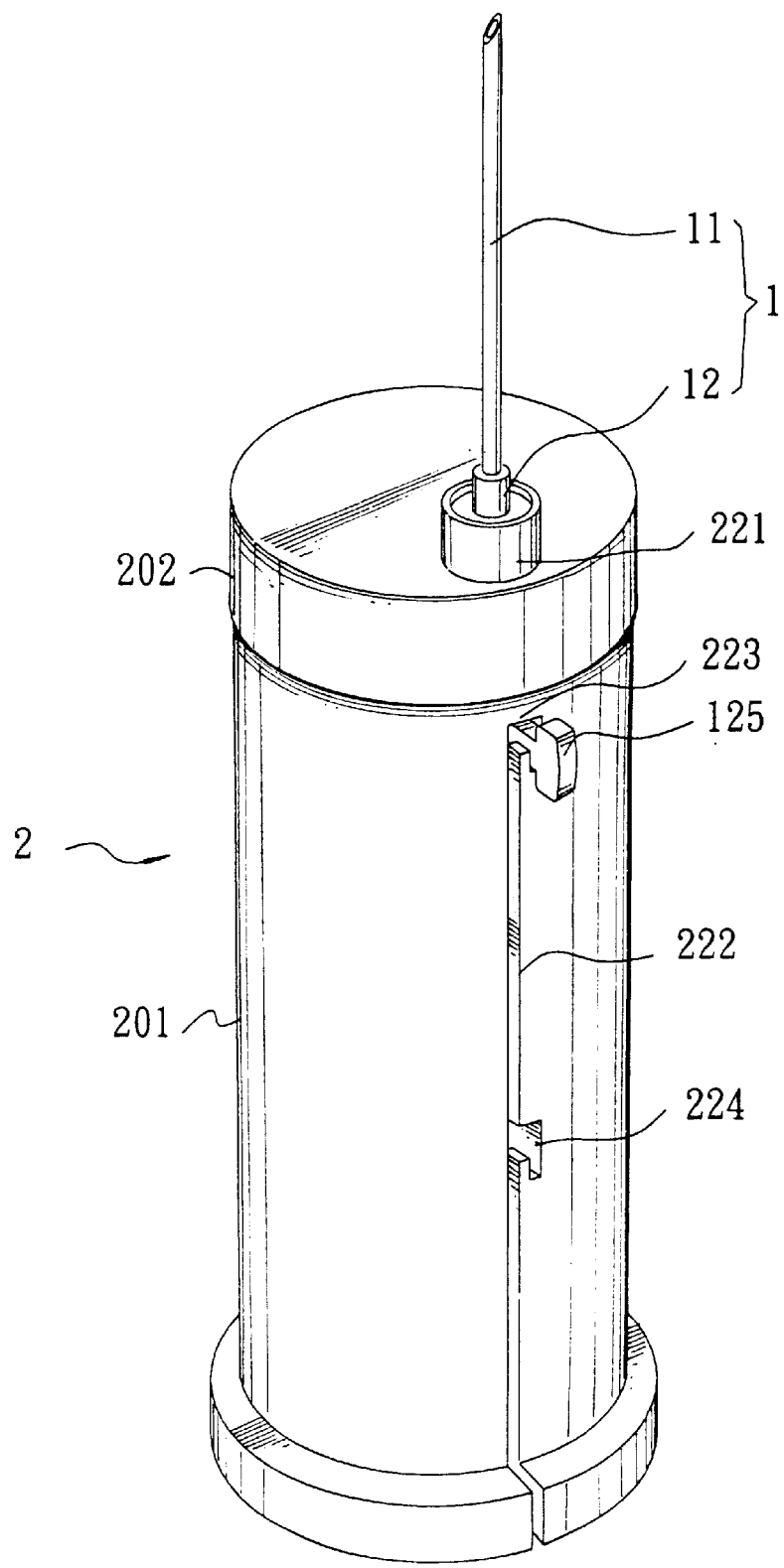
FIG. 1 is an elevational view of a dual-chamber safety hypodermis syringe according to the preferred embodiment of the present invention.

FIG. 1 is an elevational view of the preferred embodiment of the present invention, showing a needle assembly 1 installed in a barrel 2.

Figure 2:
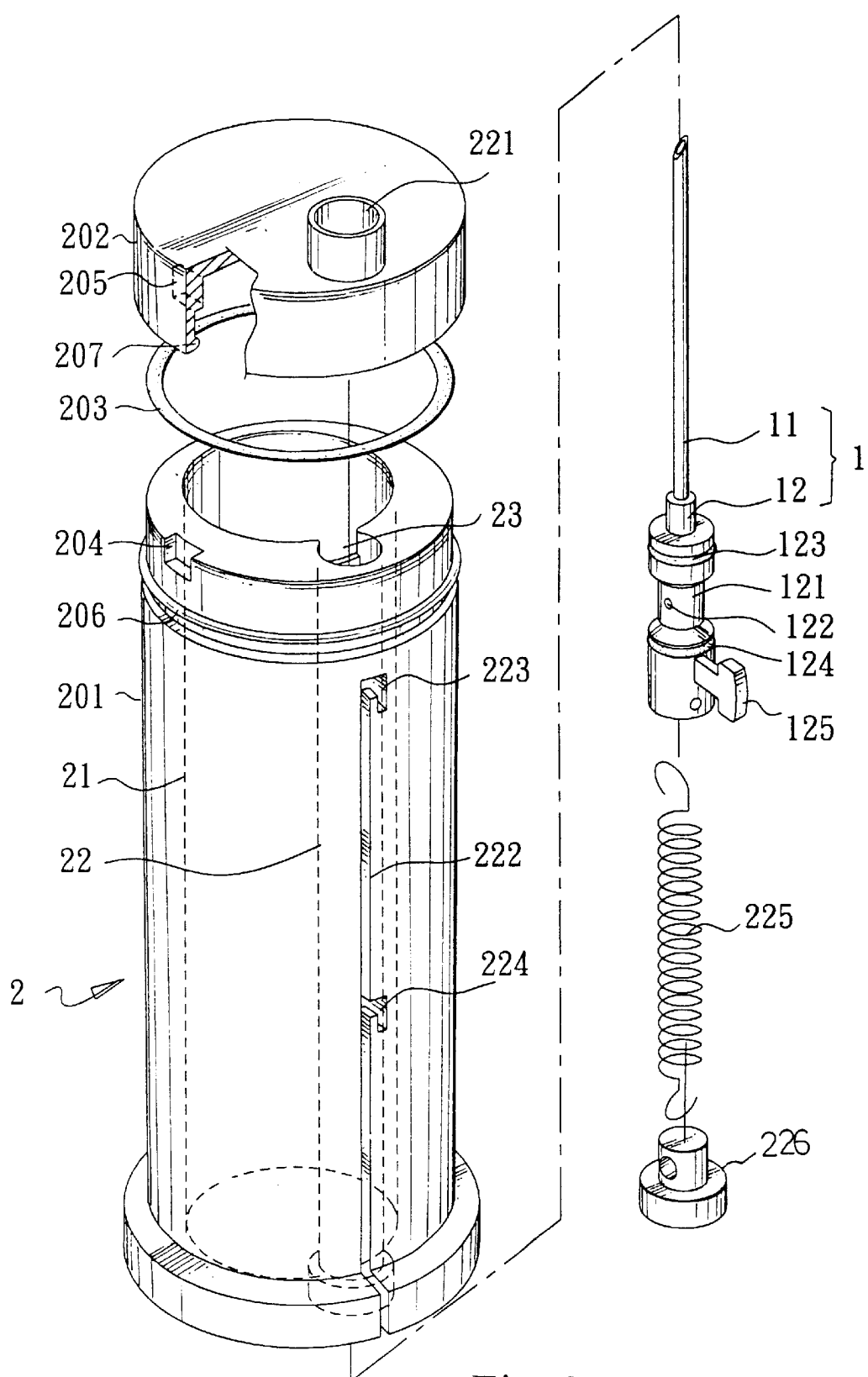
FIG. 2 is an exploded view of the dual-chamber safety hypodermic syringe according to the preferred embodiment of the present invention.

FIG. 2 is an exploded view of the preferred embodiment of the present invention. The needle assembly 1 is comprised of a needle cannula 11 and a needle hub 12 holding the needle cannula 11. The needle hub 12 is a cylindrical member that is attached to a neck 121 and an inlet 122 on the neck 121 is in communication with the inside space of the needle cannula 11. Two O-rings 123 and 124 are respectively mounted around the periphery in front of an behind the neck 121 and adapted to prevent leakage of liquid medicine or blood, and a handle 125 is perpendicularly extended from a peripheral surface of the needle hub 12.

The barrel 2 comprises a hollow cylindrical body 201, a cover 202 covered on the front side of the body 201, and an O-ring 203 sealed between the outside wall of the body 201 and the inside wall of the cover 202. The cover 202 comprises an axially extended outlet 221 in its front side, a positioning block 205 disposed on the inside, and an inwardly extended bottom coupling flange 207. The body 201 comprises an axially extended medicine chamber 21, an axially extended needle chamber 22, a top positioning notch 204, and an outside coupling flange 206 disposed around the periphery adjacent to the top positioning notch 204. By means of forcing the coupling means, i.e. coupling flange 207 of the cover 202 into engagement with the coupling flange 206 of the body 201, the body 201 and the cover 202 are coupled together. Further, when covering the cover 202 on the front side of body 201, the positioning block 205 is engaged into the positioning notch 204 to hold the cover 202 in position, keeping the outlet 221 in alignment with the needle chamber 22. As an alternate form of the present invention, the cover 202 can be fastened to the body 201 by a heat-sealing or bonding procedure. The cover 202 can also be formed integral with the body 201.

The medicine chamber 21 is adapted to hold liquid medicine or to collect blood from the patient. The cover 202 blocks the closed front side of the medicine chamber 21. The rear open side of the medicine chamber 21 is an open end into which a plunger 3 is inserted. According to the present preferred embodiment, the medicine chamber 21 has a circular cross section. Alternatively, the medicine chamber 21 can be made having an oval, heart-like or polygonal cross section. The needle chamber 22 is adapted to receive the needle assembly 1, having a front open side axially connected to the outlet 221 of the cover 202 and a rear open side fixedly sealed with a plug 226. Spring means 225 is connected between the plug 226 and the needle assembly 1, and adapted to hold the needle assembly 1 normally inside the needle chamber 22. The spring means 225 can be a tensile spring, a rubber rod, an elastic band, or any equivalent elastic material. The body 201 further comprises a longitudinal sliding slot 222 axially forwardly extended from the rear end and disposed in parallel to and in communication with the needle chamber 22, and a retaining hole, namely, the first retaining hole 223 extended sideways from the front end of the longitudinal sliding slot 222 and adapted to hold the needle assembly 1 in the extended position. After installation of the needle assembly 1 in the needle chamber 22, the handle 125 extends through the longitudinal sliding slot 222 to the outside of the body 201.

Figure 3:
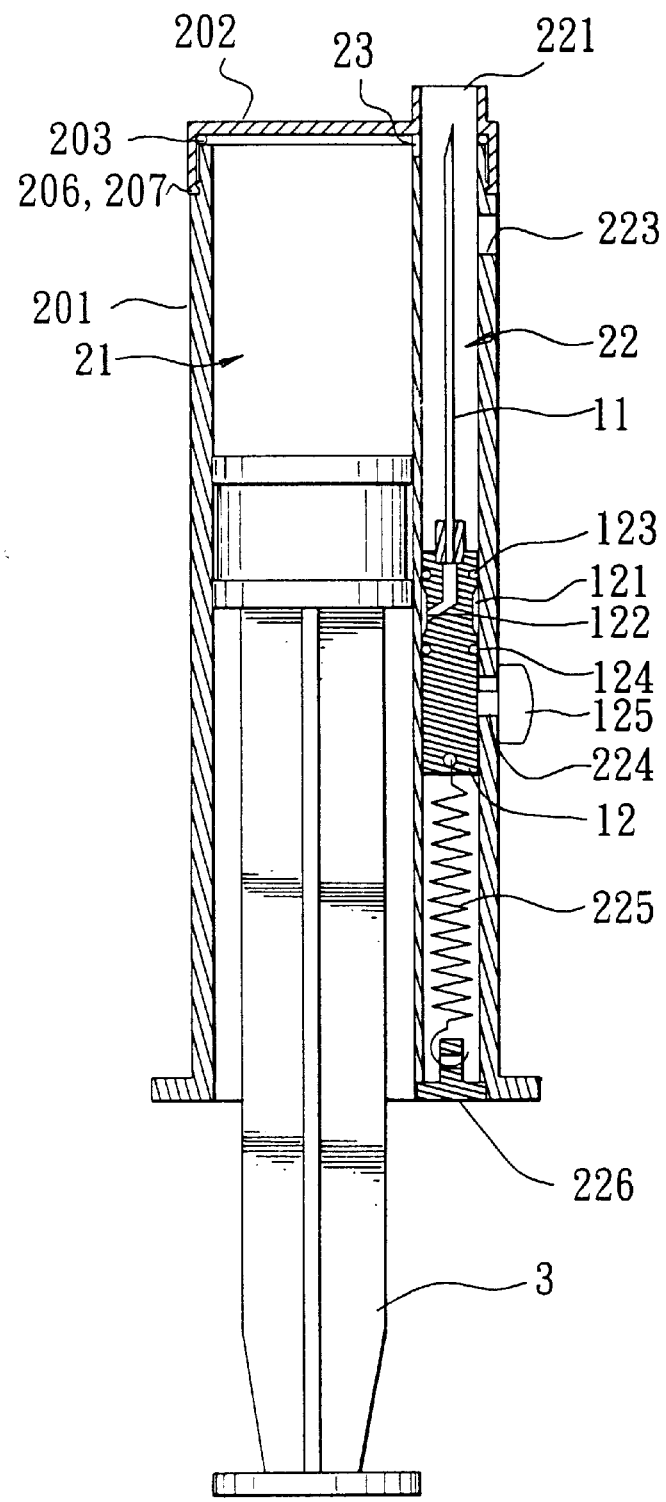
FIG. 3 is a longitudinal view in section of the present invention showing the needle assembly received inside the needle chamber of the barrel.

Referring to FIG. 3, the medicine chamber 21 and the needle chamber 22 are separated chambers that communicate with each other through a guide hole 23, which is disposed in the border area between the front side of the medicine chamber 21 of the body 201 and the cover 202. The design of the guide hole 23 enables the body 201 to be easily removed from the injection mold.

Referring to FIG. 3 again, when not in use, the spring means 225 imparts a downward pressure to the needle assembly 1, keeping the needle assembly 1 received inside the needle chamber 22. The body 201 further comprises a second retaining hole 224 extended sideways from a middle part of the longitudinal sliding slot 222 and adapted to hold the needle assembly 1 positively in the received position inside the needle chamber 22. By means of moving the handle 125 along the longitudinal sliding slot 222 to the elevation of the second retaining hole 224 and then turning the handle 125 sideways into the second retaining hole 224, the needle assembly 1 is locked in the received position inside the needle chamber 22. Alternatively, the handle 125 can be slided sideways into another tight second retaining hole to hold the needle assembly 1 tightly in its received position, the aforesaid spring means 225 and plug 226 can be eliminated.

Figure 4:
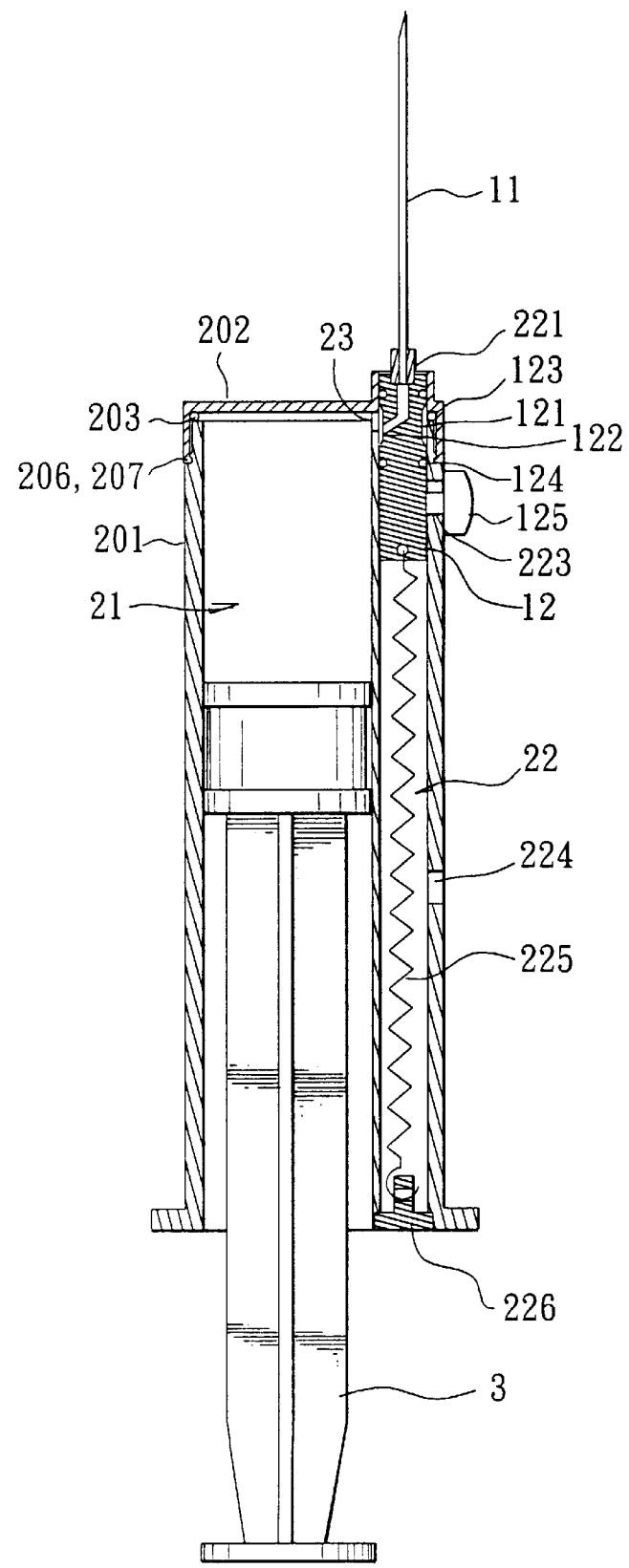
FIG. 4 is a longitudinal view in section of the present invention showing the needle cannula extended out of the outlet of the cover of the barrel.

Referring to FIG. 4, when in use, the handle 125 is disengaged from the second retaining hole 224 and moved forwards along the longitudinal sliding slot 222 to extend the needle cannula 11 out of the outlet 221 of the cover 202, and then the handle 125 is turned sideways and engaged into the first retaining hole 223 at the top end of the longitudinal sliding slot 222 to lock the needle assembly 1 in the extended (operative) position. At this time, the neck 121 of the needle hub 12 is aimed at the guide hole 23, keeping the inlet 122 in communication with the medicine chamber 21, and therefore liquid medicine is squeezed out through the medicine chamber 21, the guide hole 23, the neck 121, the inlet 122 and the needle cannula 11 when pushing the plunger 3 forwards.

After the service of the hypodermic syringe, the handle 125 is turned sideways from the first retaining hole 223 into the longitudinal sliding slot 222, and then moved downwards along the longitudinal sliding slot 222 to receive the needle assembly 1 inside the needle chamber 22, and then engaged into the second retaining hole 224 to lock the needle assembly 1 safely in the received (non-operative) position as shown in FIG. 3.

Because the plunger 3 is received in the medicine chamber 21, it can be pushed first to the front limit position in close contact with the inside wall of the cover 202 (no gap is left in front of the plunger inside the barrel). Therefore, the hypodermic syringe can be used to draw blood from the patient when pulling the plunger 3 backwards, and no special packing material is needed to pack the hypodermic syringe, which reduces package cost.

Although the present invention has been explained in relation to its preferred embodiment, it is to be understood that many other possible modifications and variations can be made without departing from the spirit and scope of the invention as hereinafter claimed.

What is claimed is:

1. A dual-chamber safety hypodermic syringe comprising:

a needle assembly, said needle assembly comprising a needle hub and a needle cannula mounted in said needle hub, said needle hub is attached to a neck and an inlet on said neck is in communication with said needle cannula, and a handle extends from a peripheral surface of said needle hub; and a barrel, said barrel comprising a front side, a rear side, a medicine chamber and a needle chamber respectively extended in an axial direction, an outlet in the front side of said barrel, said needle chamber having a front open side connected to said outlet and a rear open side extended through the rear side of said barrel, said medicine chamber having a closed front side and a rear open side extended to through the rear side of said barrel, a guide hole communicated between said medicine chamber and said needle chamber, a longitudinal sliding slot disposed in parallel to and in communication with said needle chamber, and a front retaining hole extended sideways from a front end of said longitudinal sliding slot;

wherein said needle assembly is slidably mounted in said needle chamber such that when said handle is moved forwards along said longitudinal sliding slot and engaged into said front retaining hole, said needle assembly is locked in an extended position to hold said needle cannula outside said barrel and to keep said inlet in communication with said guide hole for enabling a liquid medicine or blood to pass through said medicine chamber, said guide hole, said inlet and said needle cannula; and wherein said barrel further comprises a plug sealed to the rear open side of said needle chamber, and a spring device connected to between said plug and the needle hub of said needle assembly.

2. The dual-chamber safety hypodermic syringe as claimed in claim 1 further comprising a plurality of O-rings respectively mounted around the periphery of said needle hub and spaced front and rear sides of said neck.

3. The dual-chamber safety hypodermic syringe as claimed in claim 1, wherein said barrel further comprises a second retaining hole extended sideways from a middle part of said longitudinal sliding slot and adapted to receive said handle to hold said needle assembly in a received position received inside said needle chamber.

4. A dual-chamber safety hypodermic syringe comprising:

a needle assembly, said needle assembly comprising a needle hub and a needle cannula mounted in said needle hub, said needle hub is attached to a neck and an inlet on said neck is in communication with said needle cannula, and a handle extends from a peripheral surface of said needle hub; and a barrel, said barrel comprising a front side, a rear side, a medicine chamber and a needle chamber respectively extended in an axial direction, an outlet in the front side of said barrel, said needle chamber having a front open side connected to said outlet and a rear open side extended through the rear side of said barrel, said medicine chamber having a closed front side and a rear open side extended to through the rear side of said barrel, a guide hole communicated between said medicine chamber and said needle chamber, a longitudinal sliding slot disposed in parallel to and in communication with said needle chamber, and a front retaining hole extended sideways from a front end of said longitudinal sliding slot;

wherein said needle assembly is slidably mounted in said needle chamber such that when said handle is moved forwards along said longitudinal sliding slot and engaged into said front retaining hole, said needle assembly is locked in an extended position to hold said needle cannula outside said barrel and to keep said inlet in communication with said guide hole for enabling a liquid medicine or blood to pass through said medicine chamber, said guide hole, said inlet and said needle cannula; and wherein said barrel is comprised of a hollow body and a cover covered on a front side of said body, and said guide hole is disposed in between said body and said cover.

5. The dual-chamber safety hypodermic syringe as claimed in claim 4 further comprising at least one O-ring sealed between said body and said cover.

6. The dual-chamber safety hypodermic syringe as claimed in claim 4 further comprising an axially extended positioning notch disposed in one of said body and said cover, and an axially extended positioning block disposed in the other of said body and said cover and adapted for engaging into said positioning notch.

7. The dual-chamber safety hypodermic syringe as claimed in claim 4, further comprising coupling means respectively formed on said body and said cover for enabling said cover to be coupled to said body.

8. The dual-chamber safety hypodermic syringe as claimed in claim 4 further comprising a plurality of O-rings respectively mounted around the periphery of said needle hub and spaced front and rear sides of said neck.

9. The dual-chamber safety hypodermic syringe as claimed in claim 4, wherein said barrel further comprises a second retaining hole extended sideways from a middle part of said longitudinal sliding slot and adapted to receive said handle to hold said needle assembly in a received position received inside said needle chamber.

* * * * *